US00PP19085P2

(12) United States Plant Patent
Schräder

(10) Patent No.: US PP19,085 P2
(45) Date of Patent: Aug. 12, 2008

(54) **VARIETY OF *SUTERA* PLANT NAMED 'SUMSUT 03'**

(50) Latin Name: *Sutera cordata*
Varietal Denomination: Sumsut 03

(76) Inventor: Ralf Schräder, Karl-Leisner-Str. 15, 59348 Ludinghausen (DE)

( * ) Notice: Subject to any disclaimer, the term of this patent is extended or adjusted under 35 U.S.C. 154(b) by 0 days.

(21) Appl. No.: 11/518,778

(22) Filed: Sep. 11, 2006

(51) Int. Cl.
*A01H 5/00* (2006.01)

(52) U.S. Cl. ..... Plt./485
(58) Field of Classification Search ..... Plt./485
See application file for complete search history.

*Primary Examiner*—Kent L Bell
*Assistant Examiner*—June Hwu
(74) *Attorney, Agent, or Firm*—The Webb Law Firm

(57) ABSTRACT

A new and distinct *Sutera* plant with white colored double flowers and a long flowering season.

3 Drawing Sheets

Botanical classification: *Sutera cordata.*
Varietal denomination: 'Sumsut 03'.

BACKGROUND OF THE INVENTION

The present invention comprises a new and distinct cultivar of *Sutera* plant known by the varietal name 'Sumsut 03'. The new variety was developed in 2004 in a selected breeding program in Ludinghausen, Germany. The purpose of the breeding program was to develop a Sutera plant with a semi-erect growth habit and long flowering time in the summer. The new variety is a selection from the cross of proprietary unpatented breeding plants. The female parent was Seedling 1–5 and the male parent was Seedling 1–70. The upright to semi-upright growth character of the new variety is similar to its parents but the new variety exhibits double flowers. The new variety was first asexually reproduced in July of 2004 by tip cuttings in Germany. The new variety has been trial and field tested and has been found to retail its distinctive characteristics and remains true to type through successive asexual propagations.

The following traits distinguish 'Sumsut 03' as a new and distinct cultivar from other Sutera varieties known to the breeder.

- Double flowers;
- Upright to semi-upright growth habit; and
- Long leaves that are rounded in shape.

Further, the new variety exhibits a similar rooting habit and white flowers like Sutera variety 'Blizzard' (U.S. Plant Pat. No. PP10,996). However, 'Sumsut 03' exhibits double flowers and 'Blizzard' is a single flowering variety.

DESCRIPTION OF THE DRAWINGS

The accompanying photographic drawings illustrate the new variety, with the color being as nearly true as is possible with color illustrations of this type.

DESCRIPTION OF THE PLANT

Figure 1:
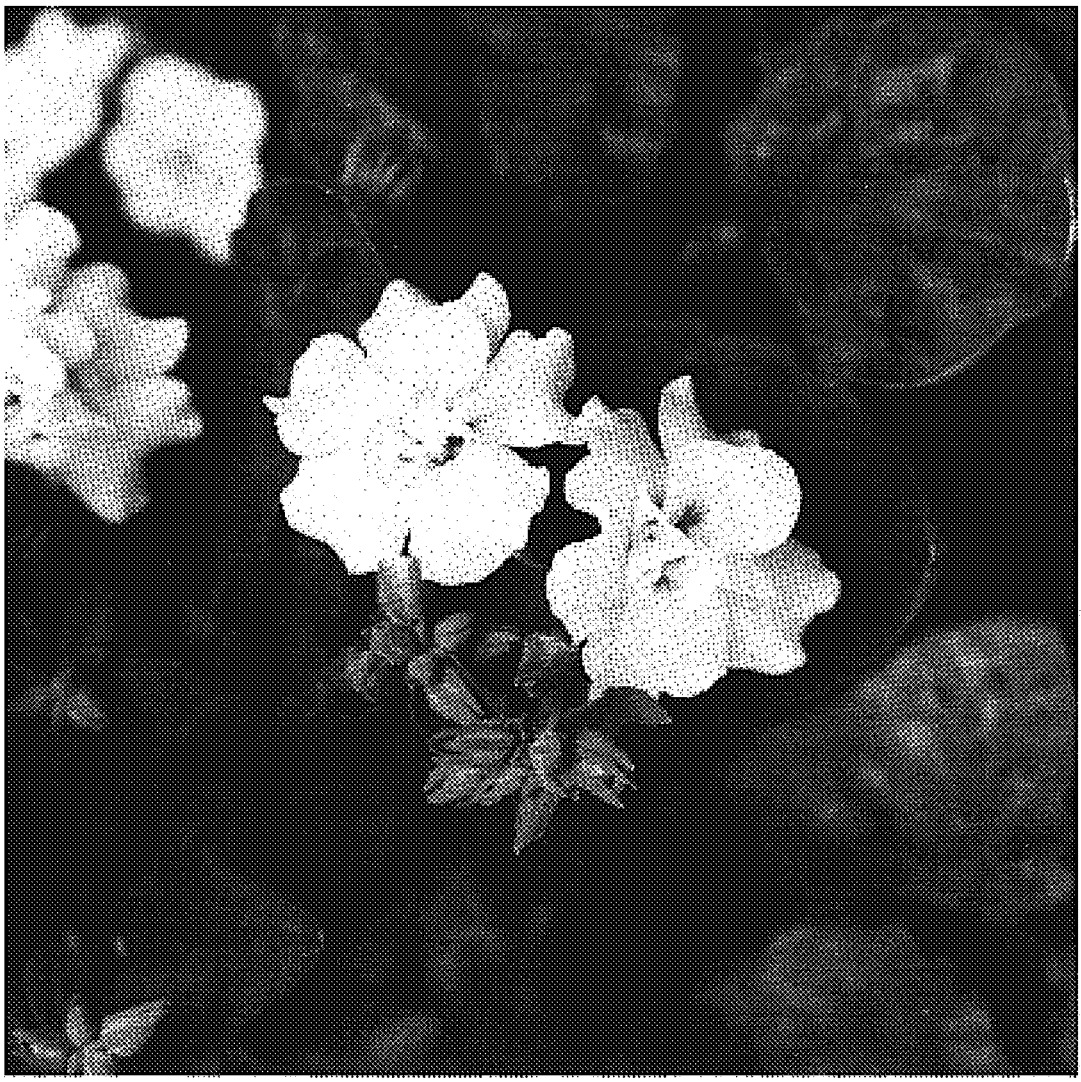
FIG. 1 is a close-up photograph of the flowers of the new variety.
Figure 2:
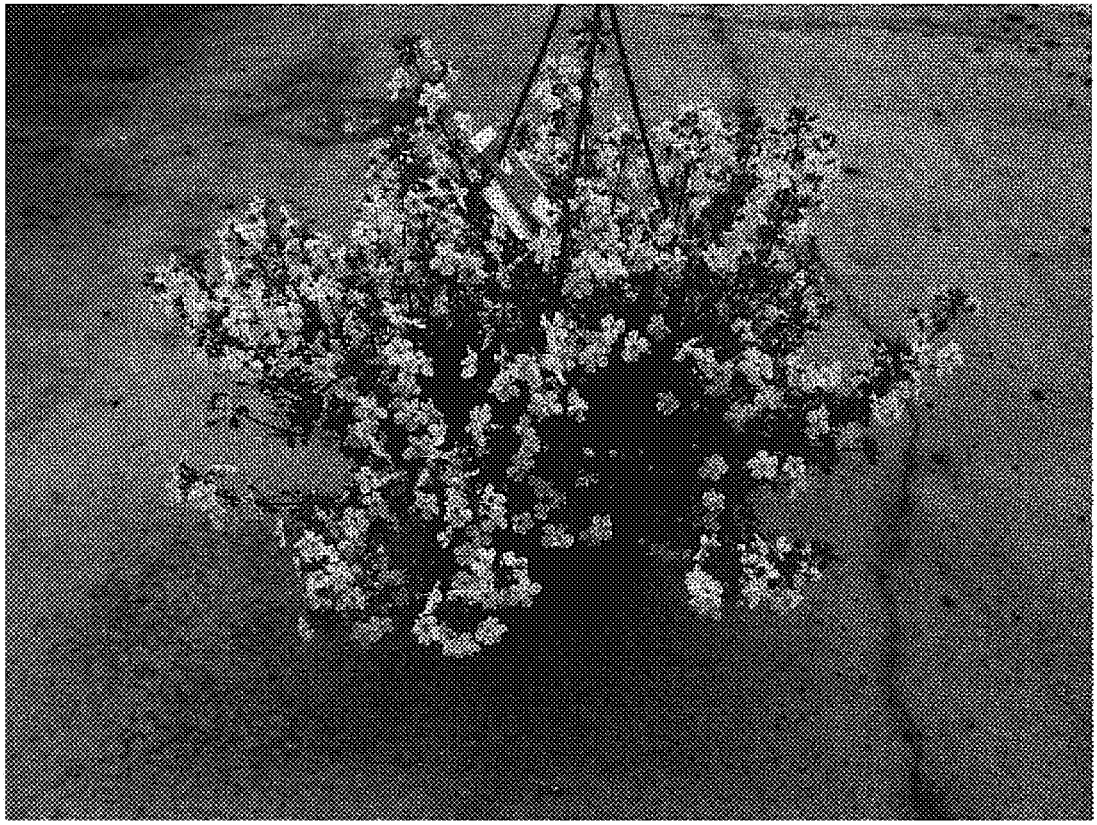
FIG. 2 is a photograph of an entire plant of the new variety.
Figure 3:
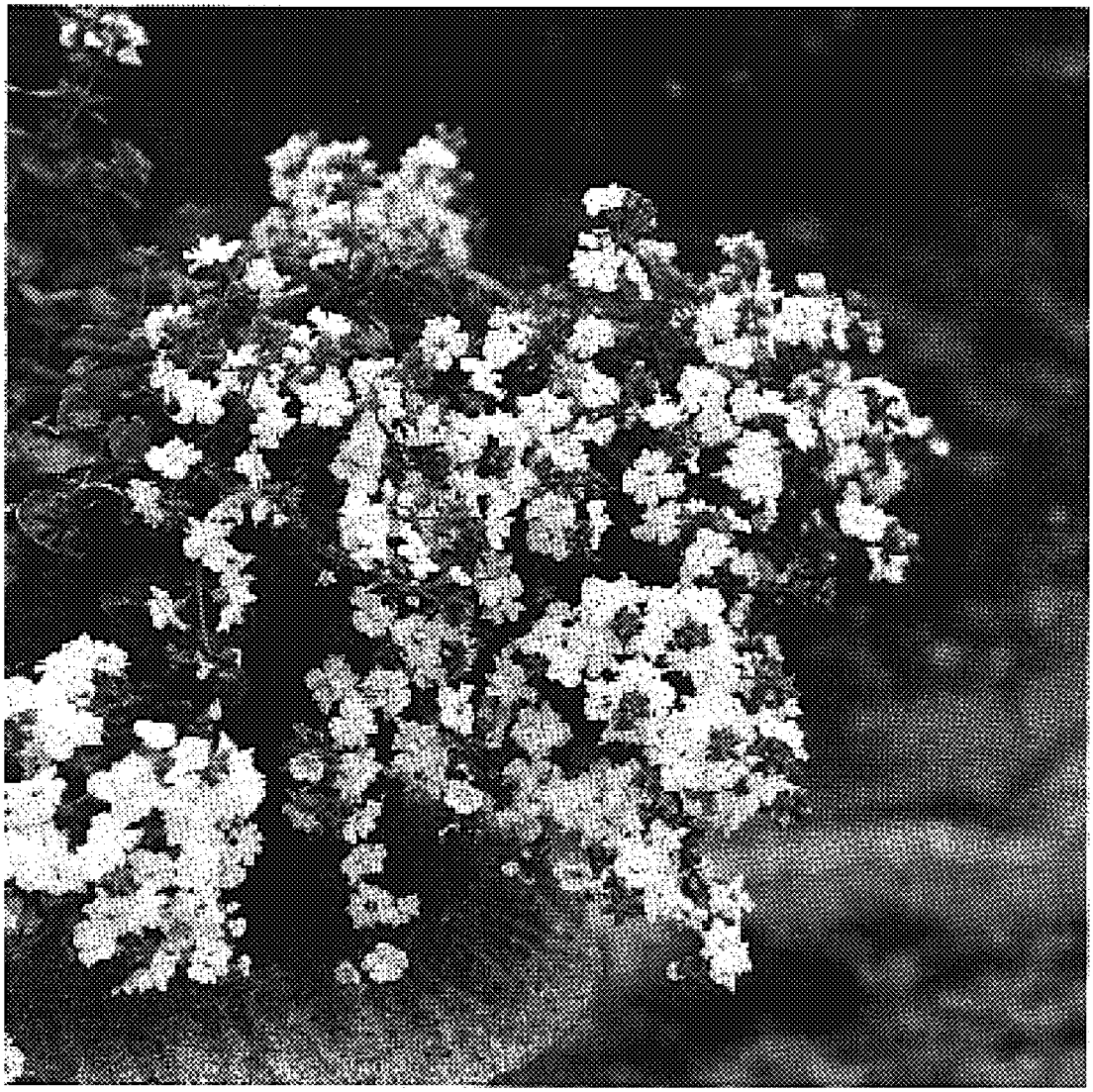
FIG. 3 is another view of the entire plant of the new variety.

The following detailed description sets forth the characteristics of the new cultivar. The data which defines these characteristics were collected by asexual reproductions carried out in Germany. Plants for the description were grown outdoors in a lined 25 cm hanging basket at 25–30° C. daytime temperatures and at 12–15° C. night temperatures. The color readings were taken on a plant outdoors on a sunny day. Color references are primarily to the R.H.S. Colour Chart of The Royal Horticultural Society of London.

PLANT

Classification:
*Botanical.*—*Sutera cordata.*
*Commercial.*—Bacopa.
Form: Semi-erect initially, followed by a half-hanging from with many branches.
Height: Approximately 25 cm from soil to top of flowers.
Diameter: Approximately 45 cm.
Growth: Vigorous.
Roots:
*Habit.*—Fine, well-branched and fibrous.
*Time to initiate roots.*—About 12 days at 17° C.
*Time to develop roots.*—About 21 days at 17° C.
Lateral branches:
*Form.*—Hanging.
*Color.*—146C to 146D.
*Texture.*—Smooth.
*Diameter.*—5–6 mm.
*Internode length.*—2–2.5 cm.
Foliage:
*Arrangement.*—Opposite.
*Number of leaves per branch.*—2 per node; approximately 20–24 per branch.
*Size of leaf.*—Length: 22–22 mm. Width: Approximately 15 mm.
*Shape of leaf.*—Ovoid.
*Shape of apex.*—Acute.
*Shape of base.*—Truncate.
*Texture.*—Upper surface: Smooth. Lower surface: Smooth.
*Aspect.*—Slightly cupped.

*Margin type.*—Crenate.
*Color.*—Young leaves: Upper surface: 137C. Lower Surface: 137D. Mature leaves: Upper surface: 137C. Lower surface: 146B.

Petioles:
*Length.*—1 mm.
*Diameter.*—1 mm.
*Color.*—137C.

Vein color: 137D.

FLOWER

Natural flowering season: April through autumn until frost; tolerates temperatures of about 2–38° C.

Flower type and habit: Double flowers that tilt slightly outward.

Number of flowers per stem: 15–20.

Fragrance: None.

Flower:
*Diameter.*—16–18 mm.
*Tube length.*—8–10 mm.
*Tube diameter.*—6 mm.
*Outer tube color.*—14D.
*Inner tube color.*—17A.

Petal:
*Length.*—6 mm.
*Width.*—5 mm.
*Margin.*—Smooth.
*Shape.*—Round.
*Texture.*—Smooth.
*Aspect.*—Rounded.
*Average number per flower.*—8–12.

Color:
*When opening.*—Upper surface: 155A. Lower surface: 155A.
*Fully opened.*—Upper surface: 155A. Lower surface: 155A.

Petaloids:
*Average number per flower.*—5.

Peduncle:
*Length.*—6–7 mm.
*Diameter.*—1 mm.
*Color.*—138A.
*Orientation.*—Outward.
*Strength.*—Very good.

Bud:
*Shape.*—Oblanceolate.
*Length.*—Approximately 5 mm.
*Diameter.*—3 mm.
*Color.*—157A.

Calyx:
*Arrangement.*—Whorled, star-like.
*Length.*—4 mm.
*Diameter.*—3 mm.
*Sepals.*—Shape: Needle; tip is acute. Margin: Entire. Outer surface texture: Smooth. Number: 5. Length: 4 mm. Width: 0.5–1 mm. Color: Upper surface: 143A. Lower surface: 143A.

REPRODUCTIVE ORGANS

Stamens:
*Number.*—4.
*Filament length.*—2 mm.
*Anthers.*—Shape: Round. Length: 1 mm. Color: 7A.
*Pollen.*—Color: 7A. Amount: Slight.

Pistils:
*Length.*—5 mm.
*Style.*—Length: 4 mm. Color: 138B.
*Stigma.*—Shape: Ovoid. Color: 138B. Ovary color: 138B.
*Seeds.*—None.

I claim:

1. A new and distinct variety of *Sutera* plant substantially as is herein described and illustrated.

* * * * *

UNITED STATES PATENT AND TRADEMARK OFFICE

CERTIFICATE OF CORRECTION

PATENT NO. : PP 19,085 P2
APPLICATION NO. : 11/518778
DATED : August 12, 2008
INVENTOR(S) : Schräder It is certified that error appears in the above-identified patent and that said Letters Patent is hereby corrected as shown below:

Column 2, Line 17, "half-hanging from" should read -- half-hanging form --

Column 2, Line 37, "Length: 22-22 mm." should read -- Length: 20-22 mm. --

Signed and Sealed this

Thirteenth Day of January, 2009

JON W. DUDAS
*Director of the United States Patent and Trademark Office*